United States Patent [19]
Chandler et al.

[11] Patent Number: 5,924,986
[45] Date of Patent: Jul. 20, 1999

[54] METHOD AND SYSTEM FOR COHERENT ULTRASOUND IMAGING OF INDUCED, DISTRIBUTED SOURCE, BULK ACOUSTIC EMISSIONS

[75] Inventors: Paul E. Chandler, Santa Cruz; John W. Sliwa, Jr., Los Altos; Sevig Ayter, Cupertino, all of Calif.

[73] Assignee: Acuson Corporation, Mountain View, Calif.

[21] Appl. No.: 08/926,513

[22] Filed: Sep. 10, 1997

[51] Int. Cl.[6] .............................. A61B 5/00; A61B 8/00
[52] U.S. Cl. ...................... 600/407; 600/437; 600/443
[58] Field of Search .................... 600/407, 437, 600/443, 587; 73/597, 602

[56] References Cited

U.S. PATENT DOCUMENTS

| | | | |
|---|---|---|---|
| 5,070,733 | 12/1991 | Nagota et al. | 73/602 |
| 5,099,848 | 3/1992 | Parker et al. | 73/575 |
| 5,170,666 | 12/1992 | Larsen | 73/571 |
| 5,402,786 | 4/1995 | Drummond | 324/318 |
| 5,476,098 | 12/1995 | O'Donnell . | |
| 5,615,675 | 4/1997 | O'Donnell . | |
| 5,623,928 | 4/1997 | Wright et al. . | |
| 5,713,356 | 2/1998 | Kruger | 600/443 |

OTHER PUBLICATIONS

"New Technique Maps the Body Electric", David Ehrenstein, Science, vol. 276, May 2, 1997, p. 681.

"Researchers create Hall effect imaging", Michael K. Robinson, Biophotonics International, Jul./Aug. 1997, pp. 34–35.

"Hall Effect Imaging", H. Wen, J. Shah and R.S. Balaban, Laboratory of Cardiac Energetics, National Heart, Lung and Blood Institute, National Institutes of Health, Bethesda, Maryland 20892, pp. 1–19 including 8 pages of drawings (Undated).

*Primary Examiner*—Francis J. Jaworski
*Attorney, Agent, or Firm*—Brinks Hofer Gilson & Lione

[57] ABSTRACT

A method and system for coherent ultrasound imaging of induced, distributed source, bulk acoustic emissions. First, bulk acoustic emissions are induced from distributed sources within an object from a single transmit event of non-acoustic energy. Next, coherent signals are stored for each of a selected number of transducer elements of a transducer array receiving the induced bulk acoustic emissions. The stored coherent signals can then be focused to form an ultrasound image. Additionally, motion of an imaged object can be detected using induced, distributed source, bulk acoustic emissions.

29 Claims, 5 Drawing Sheets

METHOD AND SYSTEM FOR COHERENT ULTRASOUND IMAGING OF INDUCED, DISTRIBUTED SOURCE, BULK ACOUSTIC EMISSIONS

BACKGROUND OF THE INVENTION

Recent medical ultrasound advances have produced ultrasound imaging systems that incorporate coherent receive beamformers. As used herein, two signals are coherent when sufficient information is stored, preserved, or maintained to enable accurate characterization of the relative amplitude and phase of the complex envelopes of the two signals. Signals from individual transducer elements, as well as signals that are summed from signals from individual transducer elements, can be coherent. Coherent receive beamformers permit post-acquisition generation of multiple lines of ultrasound data and are described in U.S. Pat. Nos. 5,476,098 and 5,623,928, the latter of which is assigned to the assignee of the present invention. These systems are still limited, however, by the need to transmit acoustic energy into the imaged object in the form of externally generated ultrasound beams (e.g., focused beams, unfocused beams, or multiple spherical or cylindrical beams from individual point or line acoustic sources, respectively). The time required for the transmitted acoustic energy to propagate through an object limits data acquisition rates and frame rates of displayed images. Data acquisition rates and frame rates are further limited in two-dimensional imaging (image planes, static or versus time), three-dimensional imaging (static volume images), and four-dimensional imaging (three-dimensional volume images versus time), where multiple transmit/receive sequences are required to collect data. Additionally, coherent beamforming techniques are sensitive to motion artifacts that are introduced during multiple transmit/receive sequences.

Another recent medical advance exploits the Hall effect to examine local conductivities of tissues and generate ultrasonic pulses within the tissue, as described in Ehrenstein, "New Technique Maps the Body Electric," Science, Vol. 276, page 681, May 2, 1997; Wen et al., "Hall Effect Imaging," Laboratory of Cardiac Energetics, National Heart, Lung and Blood Institute; and "Researchers create Hall effect imaging," Biophotonics International, pages 34–35, July/August 1997. As described in these references, when an electric field pulse is applied to an object in the presence of a strong magnetic field, regions within the object respond to the electric field with a current density proportional to the local apparent conductivity. At the interfaces between regions of differing conductivities, the current densities (and the Lorentz forces on the currents) become discontinuous. The discontinuities of the Lorentz forces result in ultrasound pulses emanating from the interfaces. The references suggest that emitted pulses and conductivity profiles can be detected with fiber-optic ultrasonic sensors and photoacoustic transducers, which avoid interference with the magnetic field. As described in Wen, these transducers receive emitted pulses when the pulses fall within the beam profile of the transducer, requiring multiple transmit events to form an ultrasound image.

There is a need, therefore, for an ultrasound imaging system and method that take full advantage of these recent medical advances.

SUMMARY OF THE INVENTION

The present invention is directed to a method and system for coherent ultrasound imaging of induced, distributed source, bulk acoustic emissions. In this method and system, with one single transmit event of non-acoustic energy, an array of coherent signals can be stored and later focused to form an ultrasound image.

According to a first aspect of the invention, a method for ultrasound imaging of induced, distributed source, bulk acoustic emissions comprises the steps of inducing bulk acoustic emissions from distributed sources within an object using a single transmit event of non-acoustic energy, storing coherent signals over a time interval for each of a selected number of transducer elements of a transducer array receiving the induced bulk acoustic emissions, and focusing the stored coherent signals to form an ultrasound image.

Bulk acoustic emissions from distributed sources can be induced, for example, by using Hall-effect induction. Also, an agent can be introduced into the object to contribute to the generation of bulk acoustic emissions in response to the single transmit event of non-acoustic energy. The agent can be characterized by a conductivity different than a conductivity of the object. Further, because distributed source bulk acoustic emissions are inherently unfocussed, electric field pulses with coded sequences can be applied to improve receive detection.

The bulk acoustic emissions from the object can be received by, for example, a linear array, a curved linear array, a 360° curved linear array, a translated array, or a two-dimensional array of ultrasound transducer elements. The two-dimensional array can be planar, non-planar, curved in at least one dimension, and/or deformable. An acoustooptic receive detector can also be used to receive the acoustic emissions.

The received acoustic emissions are then transduced into corresponding signals comprising phase and amplitude information and stored. The coherent signals are stored such that there is no distinction between at least two points along different azimuthal directions. The signals can later be focused to distinguish between at least two points along different azimuthal directions to generate a plurality of scan lines or complex acoustic responses for a set of image data points.

According to a second aspect of this invention, motion of an imaged object is detected using induced, distributed source, bulk acoustic emissions by inducing bulk acoustic emissions from distributed sources within an object using a plurality of transmit events of non-acoustic energy; storing coherent signals over a time interval for each of a selected number of transducer elements of a transducer array receiving the induced bulk acoustic emissions for each of said plurality of transmit events; and detecting motion from the stored coherent signals from each of said plurality of transmit events.

According to a third aspect of the invention, a system for ultrasound imaging of induced, distributed source, bulk acoustic emissions comprises means for inducing bulk acoustic emissions from distributed sources within an object using a single transmit event of non-acoustic energy; means for storing coherent signals over a time interval for each of a selected number of transducer elements of a transducer array receiving the induced bulk acoustic emissions; and means for focusing the stored coherent signals to form an ultrasound image.

DETAILED DESCRIPTION OF THE PRESENTLY PREFERRED EMBODIMENTS

Figure 2:
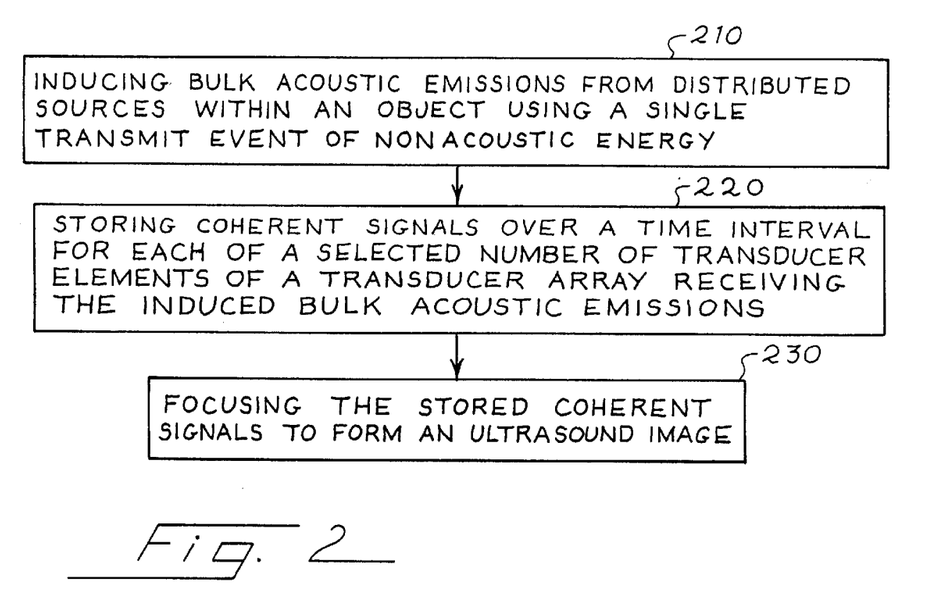
FIG. 2 is a flow chart of a method for coherent ultrasound imaging of induced, distributed source, bulk acoustic emissions.

Turning now to the figures, FIG. 2 is a flow chart illustrating a method for ultrasound imaging of induced, distributed source, bulk acoustic emissions. As shown in FIG. 2, this method comprises the steps of inducing bulk acoustic emissions from distributed sources within an object using a single transmit event of non-acoustic energy (step 210), storing coherent signals over a time interval for each of a selected number of transducer elements of a transducer array receiving the induced bulk acoustic emissions (step 220), and focusing the stored coherent signals to form an ultrasound image (step 230). These steps will be described in more detail below and in reference to FIG. 3.

As shown in FIG. 2, the first step of the method is to induce bulk acoustic emissions from distributed sources within an object (which can be, for example, a solid, semi-solid, or liquid) using a single transmit event of non-acoustic energy (step 210). While any suitable non-acoustic means can be used to induce distributed source bulk acoustic emissions from an object, it is preferred that Hall-effect induction be used. With this technique, a portion of a patient's body is placed in a magnetic field and a broadband-pulsed electric field is applied. Once pulsed, regions of local conductivity variation in the tissue act like point radiators, emitting ultrasound pulses that propagate spherically outward with an amplitude that is a strong function of the local conductivity of the tissue. The use of Hall-effect induction to induce bulk acoustic emissions is described further in Ehrenstein, "New Technique Maps the Body Electric," Science, Vol. 276, page 681, May 2, 1997, Wen et al., "Hall Effect Imaging," Laboratory of Cardiac Energetics, National Heart, Lung and Blood Institute; and "Researchers create Hall effect imaging," Biophotonics International, pages 34–35, July/August 1997, each of which is incorporated by reference.

Figure 3:
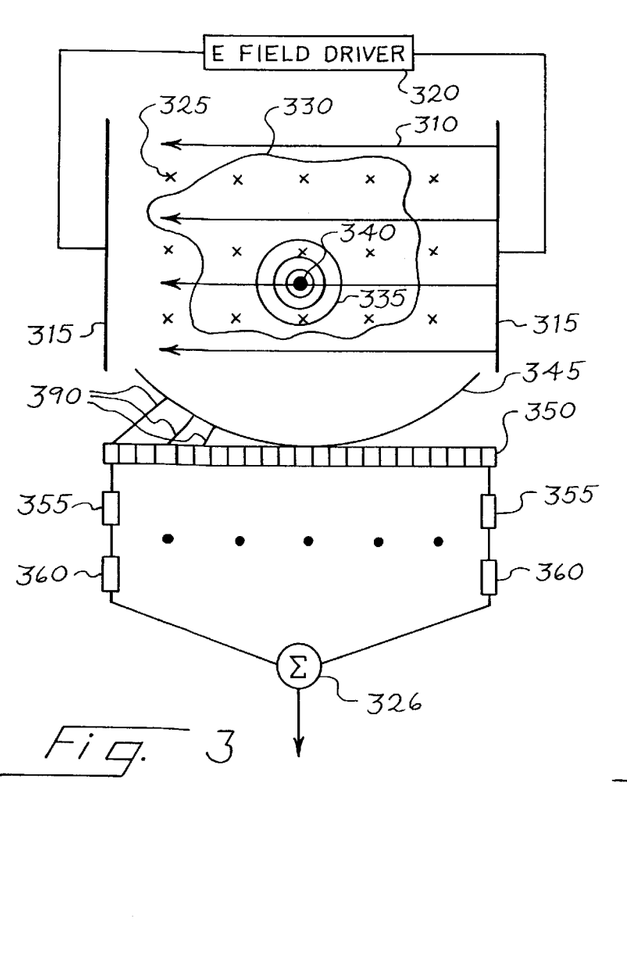
FIG. 3 is an illustration of a linear ultrasound detector of a preferred embodiment in which Hall-effect induction is used to induce distributed source, bulk acoustic emissions.

FIG. 3 shows a linear array that is used to detect Hall-effect induced bulk acoustic emissions. As shown in FIG. 3, electric field vectors 310 are generated by electric plates 315, which are driven by an electric field driver 320. A magnet (not shown) generates magnetic field vectors 325 oriented into the page. Each point of local conductivity variation in the tissue 330 emits an ultrasound pulse, although for ease of illustration, only one acoustic emission 335 emanating from one point 340 in the tissue 330 is shown. The acoustic emissions from all points in the tissue 330 form wavefronts, one of which is shown in FIG. 3 as wavefront 345.

The next step in the method is to store coherent signals over a time interval for each of a selected number of transducer elements of a transducer array receiving the induced bulk acoustic emissions (step 220). First, the acoustic emissions are received by an array transducer. Although any suitable array transducer can be used, the wavefront 345 in FIG. 3 is shown impinging on a linear array transducer 350. As shown in this figure, the wavefront 345 arrives at each element of the transducer 350 at different times, shown by distances 390. The relation between time and distance is determined by the sound velocity in the acoustic coupling medium (not shown), which acoustically couples the acoustic waves to the transducer 350. Each transducer array 350 element, which is attached to a respective independent receive channel 355, receives the wavefront 345 and transduces it into electrical signals containing both phase and amplitude information. The signals are quadrature detected, and the in-phase and quadrature signals are then digitized and stored for subsequent coherent beamformation in the receive channel 355. In this way, the signals are coherent from element to element. The stored coherent signals thus form an array of information that represents the time history of received acoustic signals for each transducer element. Because the coherent signals are stored without making a distinction between at least two points along different azimuthal directions, data can be selectively chosen from the array of signals and focused and summed to form beamformed signals at any desired point or points within an imaged region. It is important to note that said azimuthal directions can be directed from one or more than one location with respect to the face of the transducer.

The third step in the method is to focus the stored coherent signals to form an ultrasound image (step 230). Up to and through storage, no distinction or segregation in the coherent signals is made as a function of azimuthal direction or elevation direction. In this step, the stored coherent signals are reconstructed to distinguish between at least two points along different azimuthal directions by using time and phase delays 360 to affect coarse and fine focusing, respectively, of the coherent signals prior to summation in summer 326. These delays 360 are applied to the electrical signals for each element of the transducer array 350 to remove the relative arrival time differences 390 between the signals received on all elements. Alternatively, only a subset of the elements may be used, or the signals from multiple elements may be combined and processed in a single channel.

The coherent beamformer described above can generate a beamformed signal for any desired azimuthal direction or any desired point from the stored data acquired following a single voltage pulse. For example, the coherent beamformer can emulate conventional ultrasound beamforning techniques by summing a plurality of time delayed signals to produce a plurality of scan lines of ultrasound information, each scan line displaced or angled with respect to the others. The complex magnitude for each scan line can then be scan converted to grayscale and mapped to an appropriate pixel location on a display.

Because of the efficiencies of bulk storage, images need not be formed from scan lines. For example, a coherent beamformer can individually generate the complex acoustic response for a set of image data points in the tissue from the stored coherent in-phase and quadrature data. As used herein, a "set of image data points" includes one image data point or more than one image data point. The set of image data points would then be complex magnitude detected and displayed as a gray-scale pixel or voxel value. In this way, separate transmit events and scan conversion steps are not necessary. It is important to note than many other reconstruction strategies can be followed and that this example is not intended to limit the scope of this invention.

An ultrasound imaging system that can carry out the above-described method comprises means for inducing bulk acoustic emissions from distributed sources within an object using a single transmit event of non-acoustic energy, means for storing coherent signals over a time interval for each of a selected number of transducer elements of a transducer array receiving the induced bulk acoustic emissions, and means for focusing the stored coherent signals to form an ultrasound image. It is preferred that the imaging system described in U.S. patent application Ser. No. 08/432,615 filed on May 2, 1995 entitled "Method and Apparatus for Receive Beamformer System" by Wright et al., which is hereby incorporated by reference, be adapted to carry out the methods described above. Other coherent beamformers are described in U.S. Pat. Nos. 5,476,098 and 5,623,928, both of which are hereby incorporated by reference.

Figure 1:
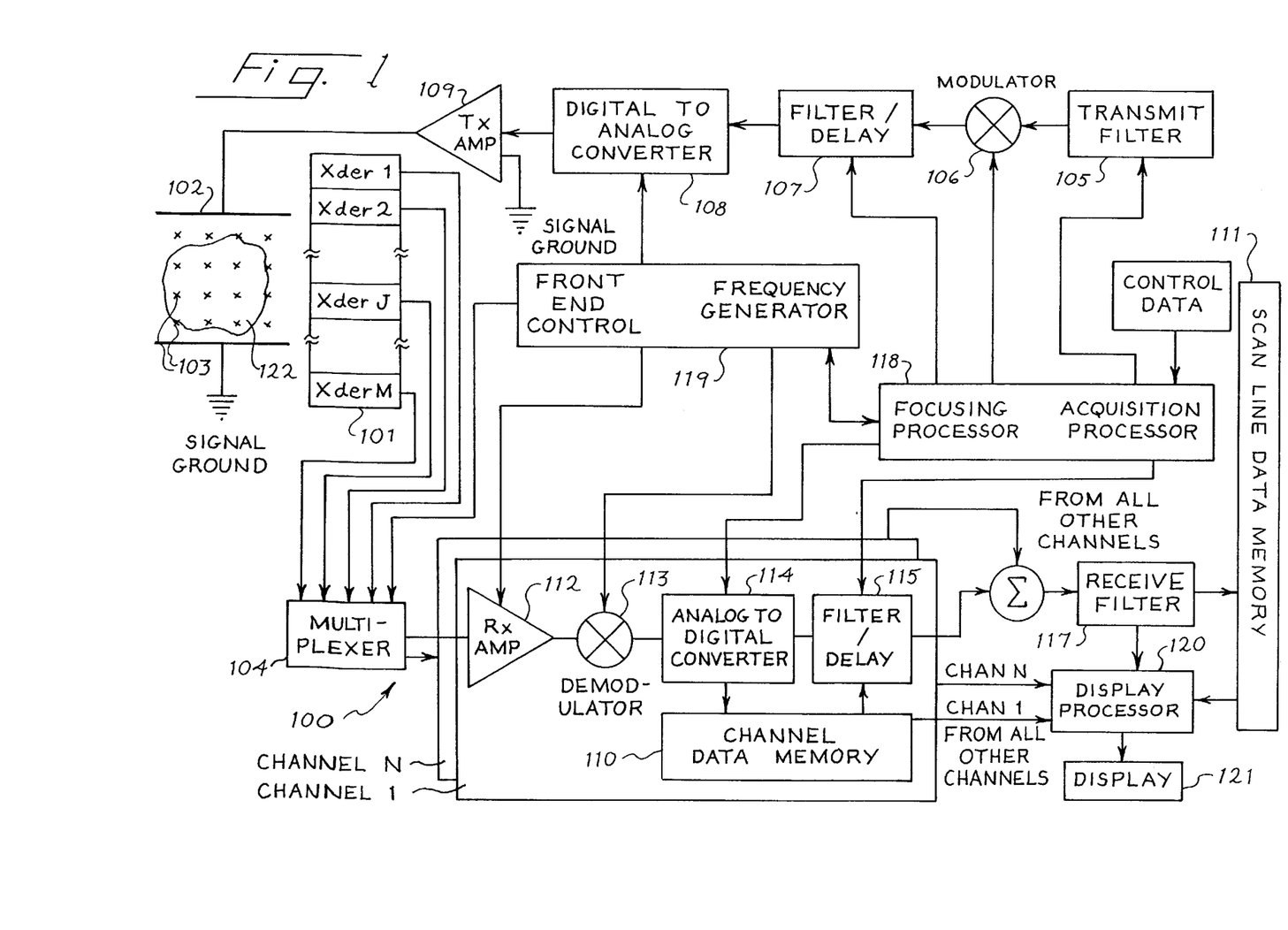
FIG. 1 is a block diagram of an ultrasound imaging system of a preferred embodiment.

FIG. 1 shows an ultrasound imaging system 100 of a preferred embodiment, although other suitable imaging systems can be used. As shown in FIG. 1, a tissue 122 is placed in a magnetic field 103 between a pair of electrodes 102 and adjacent to an acoustic array 101 of transducer elements. The electrodes 102 are driven by transmit electronics comprising a transmit filter 105 which provides the transmit signal envelope, a modulator 106 used to modulate the transmit frequency reference signal with the transmit envelope signal, a filter/delay 107, a digital-to-analog converter 108, and a transmit amplifier 109. Signals received on acoustic elements 1 to M of the array 101 are multiplexed to receive channels 1 to N by a multiplexer 104. Each of the receive channels is comprised of a receive amplifier 112, a demodulator 113, an analog-to-digital converter 114, a channel data memory 110, and a filter/delay 115. Data may be stored in the channel data memory 110 before passing through the filter/delay 115 or may be sent directly through the filter/delay 115 without first being stored. Data may be both sent through the filter/delay 115 and stored in the memory 110.

Channel data, either direct or following storage in the memory 110, can be used, for example, in any one of the following three ways. It can be sent in raw-channel-data form directly to a display processor 120 for direct conversion into display data, typically an image. It can also be sent through the filter/delay 115, a summer 116, and a receive filter 117 to the display processor 120, arriving as beamformed scanline data. Lastly, it can follow the previous path but also pass through a scan-line data memory 111 where it can be stored for later recall and possible interpolation within the display processor 120. The display processor 120 comprises all processing steps to convert raw channel data or scanline data into an image. All necessary additional filtering, demodulation, summing, scan conversion, complex interpolation, log compression, and post-processing steps are conducted within the display processor 120. Final display data is sent to the display 121 for display, typically as an image.

Coherence between the transmit side and receive side of ultrasound imaging system 100 is controlled by the front end controller and a frequency generator 119 and the focusing processor and acquisition processor 118. The ultrasound imaging system 100 is controlled via control data entering the focusing processor and acquisition processor component 118. Control data is also supplied, but not shown in FIG. 1, to the summer 116, the receive filter 117, the scan-line memory 111, and the display processor 120. The channel data 110 and scan-line data 111 memories are capable of storing in-phase and quadrature data for multiple frames of data, permitting long imaging sequences to be stored for subsequent post processing. It is important to note that, as used in this specification, "in-phase and quadrature data" is used interchangeably with "amplitude and phase information" since they describe equivalent forms of data. That is, storing in-phase and quadrature data fits the beamformer architecture better than storing phase and amplitude information, which would be calculated from the in-phase and quadrature data gained from mixing processes at demodulator 113.

Low resolution images are processed by the display processor 120 during real time data acquisition providing the operator with a low-resolution image permitting him or her to conduct the exam and collect the coherent data. Following the exam, data is read from memories 110 and/or 111 and processed into high-resolution/high-frame rate images. Static frame images are calculated directly to high resolution images.

There are several alternative embodiments of this invention. In one alternative embodiment, a coded pulse sequence is used in combination with a matched receive filter. Because distributed source bulk acoustic emissions are inherently unfocussed, it is desired to employ means to improve receive detection to compensate for the absence of transmit focus. To improve detection, it is preferred that the electric field be pulsed using coded sequences and that, following coherent beamforming, a matched filter be used to filter the receive signals to match the transmit code. This effectively recovers the equivalent of an impulsive acquisition sequence but with higher suppression of signals arising outside the intended sample volume. Matched filter methods are well known to those skilled in the art and are described in Kino "Acoustic Waves, Devices, Imaging, and Analog Signal Processing," Chapter 4, Prentice-Hall, Inc., 1987, which is hereby incorporated by reference.

Figure 4:
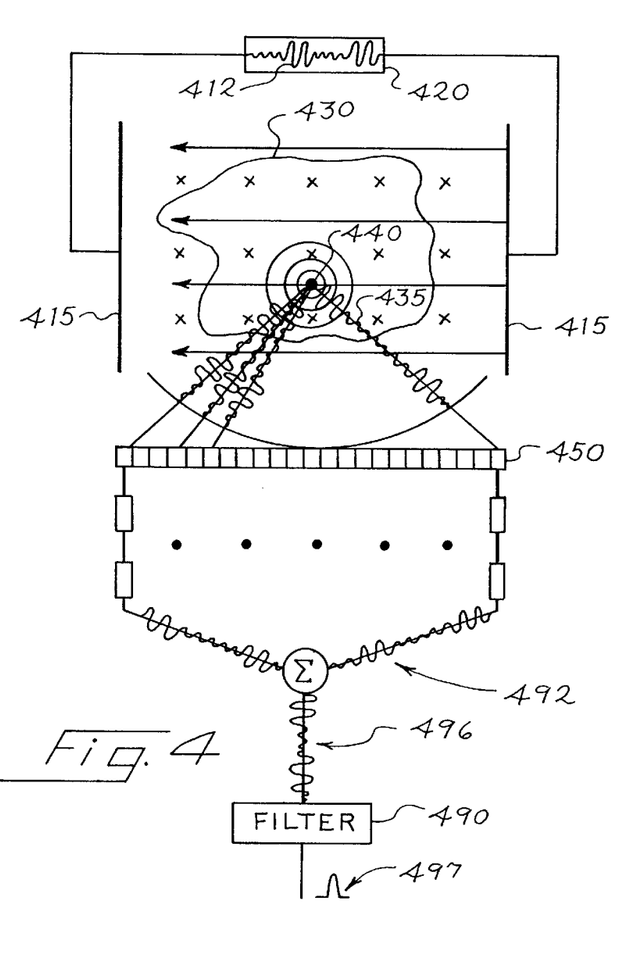
FIG. 4 is an illustration of a linear ultrasound detector of a preferred embodiment in which Hall-effect induction is used in combination with a matched filter.

FIG. 4 illustrates how matched filters can be used. FIG. 4 is virtually identical to FIG. 3 except that the electrical field driver 420 of FIG. 4 applies a coded pulse 412 to the electrical plates 415. Each point of local conductivity variation in the tissue 430 emits a coded ultrasound pulse, although for ease of illustration, only one coded pulse 435 emanating from one point 440 in the tissue 430 is shown.

Time delays are inserted during coherent beamformation and the signals 492 with the relative delay removed are summed, as described above, to produce a coded beamformer output signal 496. This signal 496 is passed through a matched filter 490 to produce the appropriate output signal 497. In this way, coded signals are coherently detected to form an amplitude modified replica of a coded pulse, but signals arriving at the array from other points in the object are not.

In another embodiment, a series of transmit/receive sequences using precisely controlled timing is used to probe the imaged object for motion. The series of inductive events induces a corresponding series of acoustic emissions from all responsive targets within the imaged object. Motion of the targets between inductive events can be detected from electrical signals acquired following each inductive event in the series. Conventional Doppler or two- or three-dimensional correlation methods can be used to detect motion along a scan line, within an image plane, or within a volume, as is well known in the art. Continuous repetition of the series permits detection and display and/or storage of one-, two-, and/or three-dimensional motion versus time.

Figure 5:
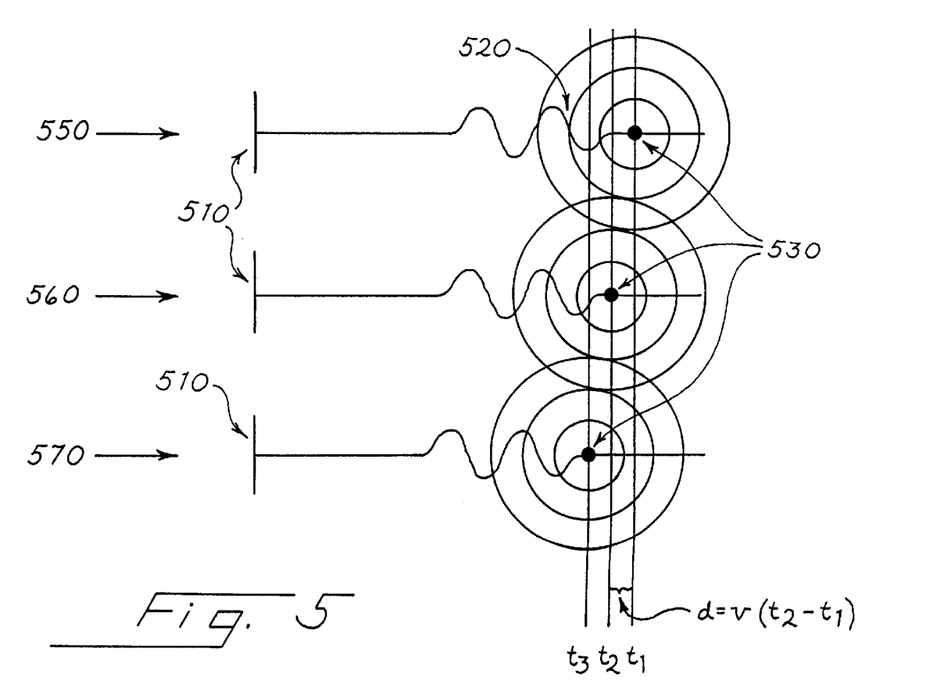
FIG. 5 is an illustration of a preferred embodiment in which motion of an imaged object is detected using induced, distributed source, bulk acoustic emissions.

This is shown in FIG. 5 where a transducer array 510 receives acoustic emissions 520 from a single moving target (i.e., a region of conductivity variation) 530 at three points in time, $t_1$, $t_2$, and $t_3$. The relative spacing between the target 530 and transducer 510 is shown in configurations 550, 560, and 570 for times $t_1$, $t_2$, and $t_3$, respectively, for the case when the target is moving toward the transducer with velocity v. Between times $t_1$, and $t_2$, this spacing shortens by distance d. It is important to note that the propagation time of the electric field variations are considered to be instantaneous in comparison to the much more slowly propagating acoustic waves. Motion information can be displayed as a Doppler waveform or Doppler image.

In another embodiment, an agent capable of contributing to the generation of bulk acoustic emissions in response to the single transmit event of non-acoustic energy can be introduced into the imaged object. The agent may be in the form of small solid, liquid, or gas bodies introduced into the blood of an imaged human patient. For Hall-effect induction, the electrical conductivity of the agent is adjusted to differ greatly from the conductivity of the adjacent body tissues.

There are several alternatives to the above-described embodiments. First, as mentioned above, non-acoustic means other than Hall-effect induction can be used to induce distributed source bulk acoustic emissions from an object, permitting tissue parameters other than conductivity to be measured.

Figure 6:
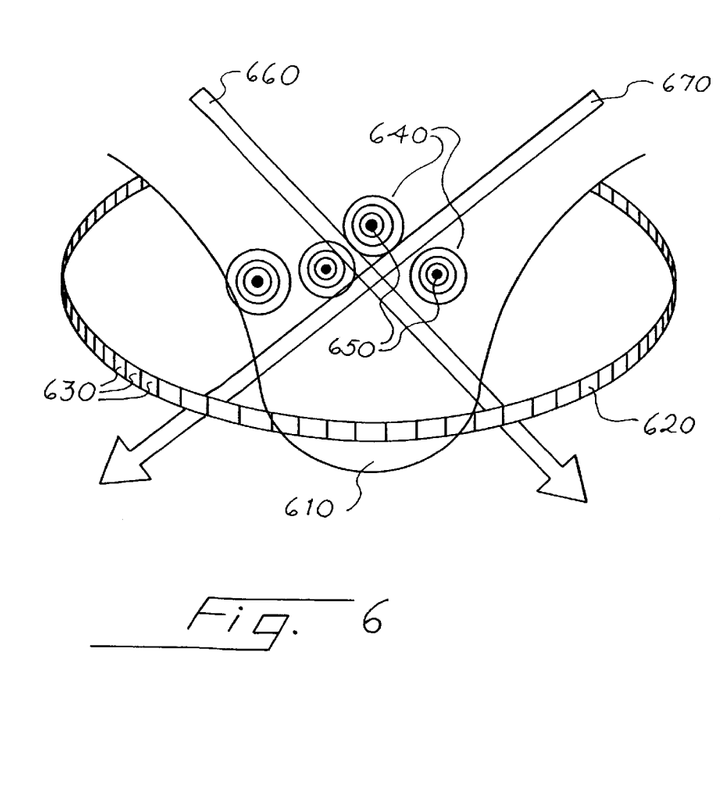
FIG. 6 is an illustration of a 360° curved linear ultrasound detector array of a preferred embodiment, which is used in combination with Hall-effect induction.

Second, while a linear array transducer was described above, other suitable transducers can be used. For example, a 360° inward-looking curved linear array which permits 360° acquisition of data from accessible body appendages such as breasts, arms, and legs can be used. As shown in FIG. 6, a human breast 610 is inserted inside a 360° inward looking curved linear array 620 having individual elements 630. Acoustic waves 640 are emitted from regions of local conductivity variation 650 within the breast 610. The magnetic field vectors 660 and electric field vectors 670 are shown in simplified form and oriented to limit interference with the acoustic transducer array. An inward-looking curved linear array can also occupy less than 360° of a perimeter of a circular or non-circular region containing the object.

Figure 7:
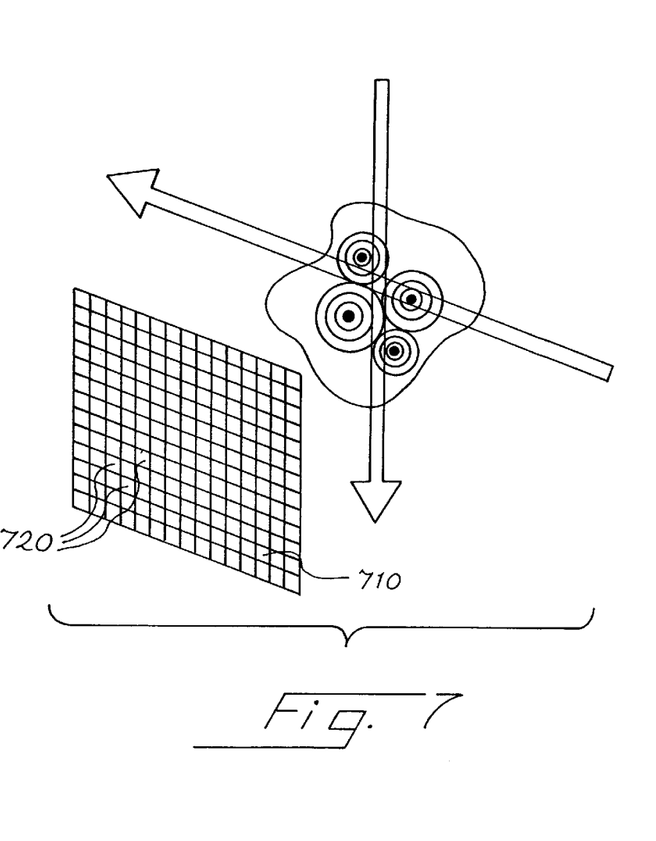
FIG. 7 is an illustration of a two-dimensional planar ultrasound detector of a preferred embodiment, which is used in combination with Hall-effect induction.

Additionally, a two-dimensional planar array can be used to acquire three-dimensional data sets in a single pulse/receive sequence. This is shown in FIG. 7, where an acoustic array 710 includes a two-dimensional array of elements 720. The two-dimensional array can be curved in one or two dimensions, and the curvature can be convex or concave in either of the two dimensions. While a fully populated array of uniformly spaced elements is depicted, it is important to note that non-uniformly spaced and/or sparse arrays, non-planar two-dimensional arrays, and deformable two-dimensional arrays can be used. An example of a deformable array is a two-dimensional PVDF array. PVDF is a common material used for receive transducers. Concern about PVDF's poor transmit sensitivity is not an issue for the preferred embodiment of this invention. Sheets of PVDF can be easily electroded, do not require dicing, and are highly flexible permitting conformance with the irregular shape of the skin surface of a patient. Approximate methods for determining the shape of the deformed arrays can be found in the literature and will not be discussed in this specification. A translated array of transducer elements can also be used.

Figure 8:
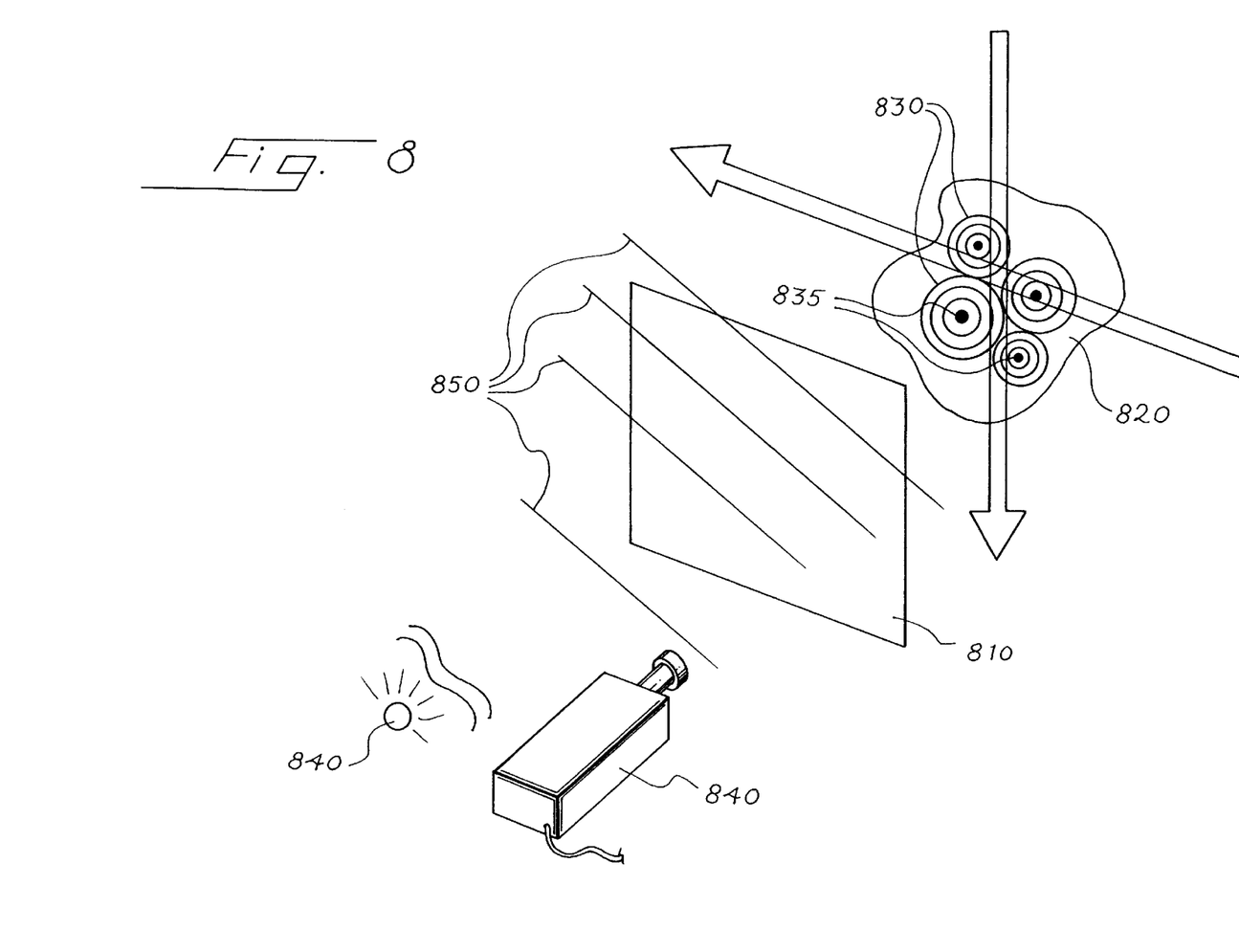
FIG. 8 is an illustration of an acoustooptic receive detector of a preferred embodiment, which is used in combination with Hall-effect induction.

An acoustooptic receive array can also be used. Use of acoustooptic sensors partially comprising unfocused optical probe beams and optical detector arrays is discussed in U.S. Pat. No. 5,615,675 to O'Donnell et al., which is hereby incorporated by reference. As shown in FIG. 8, an optically reflective sheet 810 is acoustically coupled (the coupling medium not shown) to the imaged object 820. Deformations in the reflective sheet 810 caused by the time varying acoustic wavefront 830 striking the sheet 810 can be imaged by illuminating the sheet 810 with broadly focused laser 840, which produces light wavefronts 850 that are preferably nearly planar by the time they strike the reflective sheet 810. The reflected wavefront 830 can be imaged with a suitable camera 840.

Also, when the number of array elements outnumber the available receive channels, the available receive channels can be multiplexed in blocks across the receive array for synthetic aperture formation, as described in the above-identified '098 and '928 patents. Additionally, synthetic scan lines or a set of synthetic image data points can be generated from the scan lines or set of image data points, respectively, formed from focusing the stored coherent signals.

As another alternative, multiple pulse/receive sequences can be used to record two-dimensional or three-dimension data versus time. For example, a linear or curved array can be used to acquire a plane of data during one pulse/receive sequence. The array can then be translated, fanned, or rotated before the next pulse/receive sequence, permitting a new plane of data to be acquired. The process can be repeated until a complete three-dimensional data set is acquired and can be repeated in response to a trigger derived from an EKG and/or respiration signal(s) recorded from the patient. The entire sequence can be repeated continuously or at predetermined intervals to acquire three-dimensional data sets versus time.

There are several advantages provided by these embodiments. First, an entire static two- or three-dimensional data set can be acquired in less time than with conventional ultrasound imaging systems. In conventional systems, the time required for formation of a scan line is determined in part by the time required for a transmit wave to propagate through the tissue from the transducer and the time required for the echo wave to propagate from the tissue to the transducer.

By applying non-acoustic energy to an object to induce bulk acoustic emissions, only about half the time needed to acquire an ultrasound line in conventional systems is required in the method of these preferred embodiments. For example, with Hall-effect induction, the propagation time of an electric field pulse is nearly instantaneous when compared to the much longer propagation times of the emitted acoustic waves and can typically be assumed to be instantaneous. Accordingly, acquiring the data for an ultrasound image, for example, with these preferred embodiments requires only a small fraction of the time needed to acquire data for a single image using conventional systems. Data for the entire image can be acquired with these preferred embodiments in about half the time required to acquire data for a single scan line using conventional systems.

Furthermore, when an object is induced to emit distributed source bulk acoustic waves, such that each volume element of the object is induced to simultaneously emit an acoustic wave, the characteristics of which are dependent on the inducing signal and on the local properties of the object, then, the need for multiple transmit events is removed and any static two- or three-dimensional image can be reconstructed from the data collected during a single pulse/receive sequence. Because the use of a single pulse/receive acquisition sequence effectively strobes the object to freeze motion during acquisition, a further advantage of yielding motion-artifact-free data is provided.

Because image resolution depends largely on processing time and not on acquisition time, the methods of these preferred embodiments allow image data to be quickly collected. Using this quickly collected data, low resolution, high frame rate images of moving objects can be displayed rapidly in real time during acquisition. Following acquisition, the data can be processed into high resolution, high frame rate images.

Another benefit of the invention is that induced distributed source bulk acoustic emissions contain new and different information about the local properties of the object. As described in the Ehrenstein and Wen articles cited above, because emission amplitude is a strong function of the local conductivities of a tissue, distributed source bulk acoustic emissions induced by the Hall-effect contain information about conductivity variations in a tissue. These variations can be used to distinguish tumors, fatty plaques, or areas of ischemia from normal tissue—distinctions which are typically difficult to image with conventional imaging systems. In this way, imaging using the above-described methods may be more diagnostic than conventional ultrasound for some diseases.

It is intended that the foregoing detailed description be understood as an illustration of selected forms that the invention can take and not as a definition of the invention. It is only the following claims, including all equivalents, that are intended to define the scope of this invention.

What is claimed is:

1. A method for ultrasound imaging of induced, distributed source, bulk ultrasonic pulses comprising the steps of:
   (a) inducing bulk ultrasonic pulses from distributed sources within an object using a single transmit event of electromagnetic energy; then
   (b) storing infocussed coherent signals over a time interval for each of a selected number of transducer elements of a transducer array receiving the induced bulk ultrasonic pulses; and then
   (c) focusing the stored unfocused coherent signals to form an ultrasound image.

2. The method of claim 1, wherein the coherent signals stored in step (b) make no distinction between at least two points along different azimuthal directions and wherein the focusing in step (c) reconstructs the stored unfocused coherent signals to distinguish between at least two points along different azimuthal directions.

3. The method of claim 1, wherein step (a) comprises the step of using Hall-effect induction to induce bulk ultrasonic pulses from regions of conductivity variations in the object.

4. The method of claim 1, wherein the transducer array in step (b) comprises a linear array of ultrasound transducer elements.

5. The method of claim 1, wherein the transducer array in step (b) comprises a curved linear array of ultrasound transducer elements.

6. The method of claim 1, wherein the transducer array in step (b) comprises a 360° curved linear array of ultrasound transducer elements.

7. The method of claim 6, wherein the array occupies less than 360° of a perimeter of a region containing the object.

8. The method of claim 1, wherein the transducer array in step (b) comprises a two-dimensional array of ultrasound transducer elements.

9. The method of claim 8, wherein the two-dimensional array is planar.

10. The method of claim 8, wherein the two-dimensional array is non-planar.

11. The method of claim 8, wherein the two-dimensional array is curved in at least one dimension.

12. The method of claim 8, wherein the two-dimensional array is deformable.

13. The method of claim 1, wherein the transducer array in step (b) comprises a translated array of ultrasound transducer elements.

14. The method of claim 1, wherein the transducer array in step (b) comprises an acoustooptic receive detector.

15. The method of claim 1, wherein step (c) comprises the step of using time delays to focus the stored unfocused coherent signals to form an ultrasound image.

16. The method of claim 1, wherein step (c) comprises the step of using phase shifts to focus the stored unfocused coherent signals to form an ultrasound image.

17. The method of claim 1, wherein step (c) comprises the step of focusing the stored unfocused coherent signals to form scan lines.

18. The method of claim 17 further comprising the step of synthesizing synthetic scan lines from the scan lines formed from focusing the stored unfocused coherent signals.

19. The method of claim 1, wherein step (c) comprises the step of focusing the stored unfocused coherent signals to generate a complex acoustic response for a set of image data points from the stored unfocused coherent signals.

20. The method of claim 19, wherein said set of image data points comprises one image data point.

21. The method of claim 19 further comprising the step of synthesizing a set of synthetic image data points from said set of image data points.

22. The method of claim 1, wherein step (a) comprises the step of applying an electric field pulse with a coded sequence to the object and wherein step (b) comprises the step of applying a filter matched to said coded sequence.

23. The method of claim 1, wherein step (a) comprises the step of introducing an agent to the object, said agent contributes to generation of bulk ultrasonic pulses in response to the single transmit event of electromagnetic energy.

24. The method of claim 23, wherein the agent is characterized by a conductivity different than a conductivity of the object.

25. The method of claim 1, wherein said object is a human body.

26. A method of detecting motion of an imaged object using induced, distributed source, bulk ultrasonic pulses comprising the steps of:
   (a) inducing bulk ultrasonic pulses from distributed sources within an object using a plurality of transmit events of electromagnetic energy;
   (b) storing unfocussed coherent signals over a time interval for each of a selected number of transducer elements of a transducer array receiving the induced bulk ultrasonic pulses for each of said plurality of transmit events; and
   (c) detecting motion from the stored unfocused coherent signals from said plurality of transmit events.

27. A system for ultrasound imaging of induced, distributed source, bulk ultrasonic pulses comprising:
   means for inducing bulk ultrasonic pulses from distributed sources within an object using a single transmit event of electromagnetic energy;

means for storing unfocussed coherent signals over a time interval for each of a selected number of transducer elements of a transducer array receiving the induced bulk acoustic emissions; and means for focusing the stored unfocused coherent signals to form an ultrasound image.

28. The invention of claim 27, wherein said means for storing comprises a memory for storing signals fully representative of an ultrasonic pulse received during a time interval from the transducer array, and wherein said means for forming comprises means for applying a time delay to signals stored in the memory.

29. The invention of claim 27, wherein said means for storing comprises a memory for storing signals fully representative of an ultrasonic pulse received during a time interval from the transducer array, and wherein said means for forming comprises means for applying a phase shift to signals stored in the memory.

* * * * *

UNITED STATES PATENT AND TRADEMARK OFFICE
CERTIFICATE OF CORRECTION

PATENT NO. : 5,924,986
DATED : July 20, 1999
INVENTOR(S) : Paul E. Chandler et al.

It is certified that error appears in the above-identified patent and that said Letters Patent is hereby corrected as shown below:

On the Title Page

In column 1, line 6, under "U.S. PATENT DOCUMENTS", please change "4/1997 O'Donnell" to --4/1997 O'Donnell et al.--

In column 4, line 51, please change "beamforning" to --beamforming--.

In column 7, line 9, please delete "," (comma) after "$t_1$".

In column 8, line 22, please change "dimension" to --dimensional--.

In the Claims

In claim 1, line 6, please change "infocussed" to --unfocussed--.

Signed and Sealed this

Nineteenth Day of September, 2000

Attest:

Q. TODD DICKINSON

*Attesting Officer*   *Director of Patents and Trademarks*